United States Patent [19]

Issenmann

[11] 4,266,277
[45] May 5, 1981

[54] CHROMATOGRAPHIC ANALYSIS OF GASEOUS MATTER

[75] Inventor: Olivier Issenmann, Lamorlaye, France

[73] Assignee: Compagnie Geofinanciere, Paris, France

[21] Appl. No.: 32,884

[22] Filed: Apr. 24, 1979

[30] Foreign Application Priority Data

Apr. 25, 1978 [FR] France .............................. 78 12138

[51] Int. Cl.³ .............................................. G06F 15/34
[52] U.S. Cl. ................................... 364/498; 73/23.1; 364/573
[58] Field of Search ............... 364/498, 497, 499, 573; 73/23.1; 23/230 R; 422/89

[56] References Cited

U.S. PATENT DOCUMENTS

| | | | |
|---|---|---|---|
| 3,488,480 | 1/1970 | Stacy | 364/497 |
| 3,562,501 | 2/1971 | Mears | 364/497 |
| 3,662,163 | 5/1972 | Miller et al. | 364/573 X |
| 3,676,649 | 7/1972 | Burk | 364/497 |
| 3,721,813 | 3/1973 | Condon et al. | 364/497 |
| 3,732,411 | 5/1973 | Galeener | 364/497 |
| 3,733,474 | 5/1973 | Edwards et al. | 364/497 X |
| 3,748,446 | 7/1973 | Gass et al. | 364/497 X |
| 3,860,393 | 1/1975 | Campen, Jr. | 364/497 X |

Primary Examiner—Edward J. Wise
Attorney, Agent, or Firm—Wenderoth, Lind & Ponack

[57] ABSTRACT

A method and apparatus for processing the signal produced by the detector of a chromatographic analysis apparatus, wherein the detector signal is monitored over a fixed period of time, so spaced from a "start" time origin as to include the approach to and fall from maximum concentration of one gaseous constituent flowing through the detector, and wherein the signal strength indicative of the maximum concentration of the constituent within the time period is detected and stored in an afferent index memory and the stored value of the signal is utilized to generate a value directly representative of the proportion of the constituent attaining maximum value within the time period.

17 Claims, 12 Drawing Figures

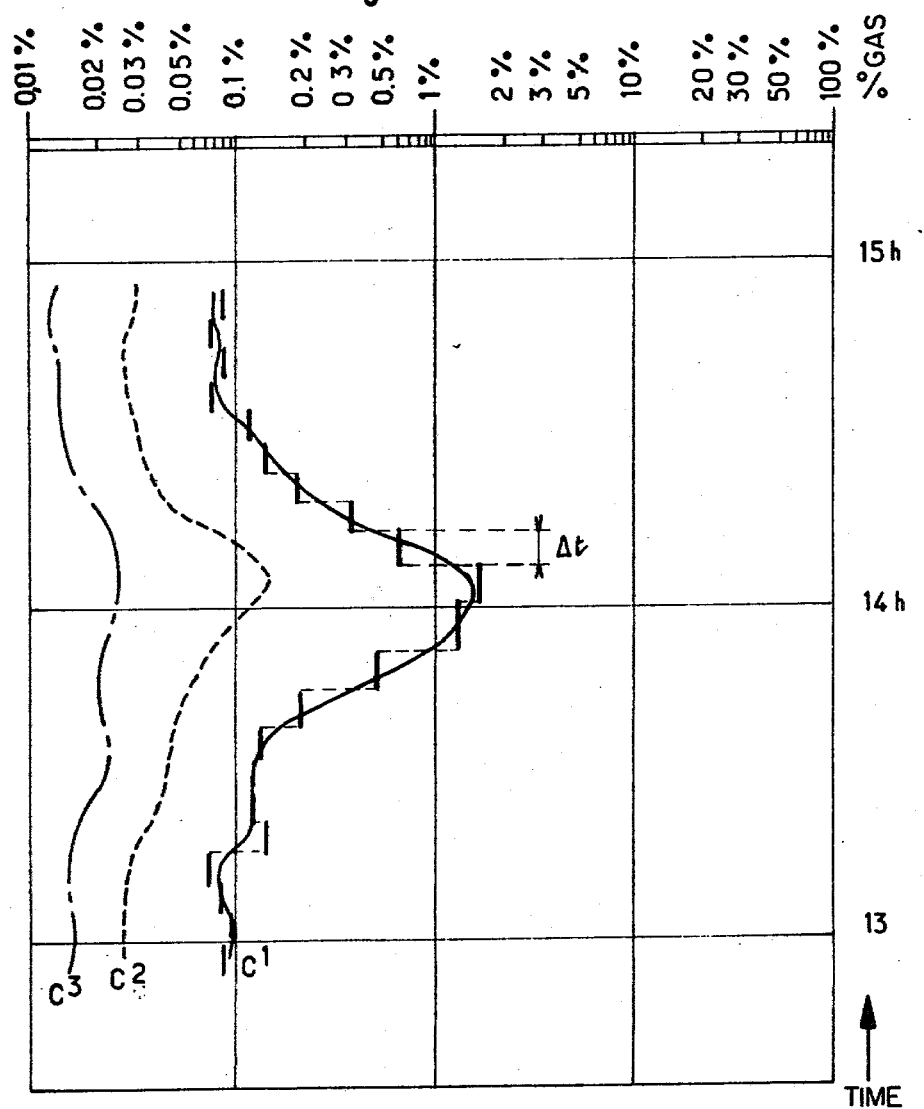

CHROMATOGRAPHIC ANALYSIS OF GASEOUS MATTER

BACKGROUND OF THE INVENTION

1. Field of Invention

This invention relates to the chromatographic analysis of gaseous matter and more particularly to the processing of data obtained by chromatographic analysis.

2. Description of Prior Art

It is well known in the art to analyze gaseous matter by driving a sample of the gaseous matter through a material which delays the passage of the constituents of the matter in accordance with their molecular masses so that the constituents exhaust from the material in increasing order of molecular mass. For some gaseous matters, for example natural gas, it is known to provide two "columns" or materials which are put in turn in circuit to separate, on one hand, the methane from the other light gases and, on the other hand, the $C_2$ to $C_4$ and possibly the $C_5$ hydrocarbons.

Apparatus for chromatographic analysis conventionally includes a detector, downstream of said material, sensitive to the passage of constituents therethrough, and which generates a signal varying in intensity in direct dependence upon the intensity of constituent flow through the detector. Such a chromatographic analysis apparatus is, hereinafter, referred to as "analysis apparatus of the type defined".

In conventional chromatographic analysis, the output from the detector is linked to a graph writing means, the intensity of the signal dictates the displacement of the graph writing means from a base line and, by traversing a graph recording medium at constant speed in a direction at right angles to the graph writing means, a representation of constituent intensity with respect to time is obtained with the different constituents in their order of exhaust through the detector. Thus, the result of a conventional chromatographic analysis is a graph comprising various peaks, each corresponding to a constituent of the gaseous matter, and the height of each peak above the base line reading is a function of the concentration of that particular constituent.

The interpretation of a chromatographic analysis in graph form as described above requires a series of manual operations as follows:

(a) Identification of each constituent, achieved by measuring the "time" distance between each peak and a "start" point on the graph indicative of a point in time before the gaseous matter was first subjected to the separating material.

(b) Measurement of the height of each peak.

(c) Assignment of each measured height of a calibration co-efficient corresponding to the nature of the constituent.

(d) Calculation of the quantity or percentage of each constituent according to the signal (conventionally an analogue signal) provided by the detector.

(e) Recordal of the values obtained for each, or selected, constituents.

The above procedure involves a relatively delicate and time consuming operation and requires specialized skill in the interpretation and calculation from the graphic display.

SUMMARY OF THE INVENTION

The present invention seeks to provide a method and apparatus for the automatic interpretation of the signal provided by the detector of a chromatograph i.e. determining the nature and concentrations of the constituents of the mixture submitted for analysis, and storing this data so that it may be read permanently by a graphic recording device, by a computer using said data, or by other processing, display or recording systems.

According to the present invention there is provided a method for processing the signal produced by the detector of a chromatographic analysis apparatus of the type defined, characterized by the steps of monitoring the detector signal obtained during a sample analysis over a fixed period of time, so spaced from a "start" time origin as to include the approach to and fall from maximum concentration of one gaseous constituent flowing through the detector, detecting the maximum signal amplitude indicative of the concentration of the constituent within said time period, storing said maximum value signal in an afferent index memory, and utilizing said stored maximum value signal to supply a value directly representative of the proportion of the constituent which gives a peak within said time period.

Preferably the method includes the steps of monitoring the detector signal over a plurality of time periods during a sample analysis, said time periods being differently spaced from the "start" time origin, whereby the approach to and fall from maximum concentration of a plurality of constituents passing through the detector occur during different time periods, detecting the maximum signal output for each constituent during its respective time period and processing said signal changes to supply values directly representative of the proportions of the detected constituents in the gaseous matter sample tested.

In a preferred embodiment the detector supplies analogue signal and the method includes the steps of digitalizing each detected signal indicative of a maximum concentration of a constituent, transmitting the digitalized signal by way of a comparison loop to a digit register and applying said digitalized signal after transformation into an analogue signal at regular intervals to one or more analogue memories used for supplying a signal indicative of the proportion of each constituent to a processing, display or recording system.

The invention also envisages apparatus for processing the detector signal of a chromatographic analysis apparatus of the type defined comprising a timing and programming device for initiating and terminating a time period whilst the detector is transmitting a signal indicative of the concentration of a constituent to be measured, a device for measuring and storing a detector maximum signal indicative of the concentration of a constituent to be measured, an analogue memory relating to said constituent to be measured, a device for calibrating and linearizing the signal of the memory and means for expressing the processed signal.

When the apparatus is to be used with a chromatographic analysis apparatus including two columns for gas analysis, the apparatus preferably includes means for correcting the zero of the detector at the start of analysis from each column. In such an embodiment the columns are preferably switched by an inverting relay which, controlled in dependence upon a gate, controls electromagnets with the aid of "AND" gates connected to the programming device and said relay at the same time ensures selection of a different length of cycle for each column, an inverter being provided between an input of the "AND" gate and the relay.

Preferably the apparatus includes a circuit for detecting an incorrect location of the time period and for indicating such an incorrect location.

In a preferred embodiment the programming device comprises a countour having ten outputs, a counter having six outputs and a counter having two or four outputs, and supplies the voltage for opening and closing the time periods by way of a decoder to five pairs of "AND" gates, said programmer being connected to an oscillator by means of a divider which controls the memory conversion circuits.

Preferably the decoder is connected with switches, which control the switching on of lights for each time period opening, to an "OR" gate which supplies a "conversion order" signal permitting measurement of the maximum amplitude of the signal indicative of the concentration of constituents, and further to one of the inputs of "AND" gates whose output is connected to an "OR" gate which, at each closure of a time period, supplies the order to store the converted signal value in the memory and actuates the timing unit.

In a preferred embodiment the device for measuring and storing the maximum value of the detector signal indicative of the concentration of a constituent comprises a single digital-analogue converter, which effects the conversions for all the detected constituents, said converter being inserted in a comparison loop connected to the analogue memories and comprising a comparator amplifier, an "AND" gate receiving a pilot frequency f/2 of a divider connected to an oscillator of the programmer, an 8-bit counter, a switch connected to a buffer register and an amplifier serving as an impedance converter for supplying the comparator amplifier and analogue memories (one for each constituent to be measured) controlled by de-multiplexers.

Preferably, the linearization of the signal available at the output of analogue memories is effected by an amplifier whose gain is adjusted as a function of the exponent p determined experimentally as a function of the response which is supplied by the logarithmic amplifier for balancing the signal and which takes the form $$\log y = p \log x$$

y being the response of the detector and x being the percentage of the constituent detected in the corresponding window.

In a preferred embodiment, the circuit for indicating the incorrect location of time periods from the time origin and which has terminals connected respectively to lines supplying the reference signal and the signal passing from the logarithmic amplifier to the inputs of the comparator of the comparison loop, comprises a comparator which supplies a comparison signal to one of the "NAND" gates whose other input receives, by way of a terminal connected to the output of the "AND" gate, the signal for storing the measured maximum value of the corresponding constituent; the comparison signal supplied by the comparator is also being supplied by an inverter to one of the inputs of another "NAND" gate whose other input receives the conversion order by way of the terminal connected to the output of the "OR" gate, the outputs of the "NAND" gates being in turn connected to the inputs of a third "NAND" gate which supplies an alarm signal.

In a preferred embodiment, means are provided for the interpretation of the signal supplied by the detector of a chromatograph, characterized in that it comprises, in combination and in association with a chromatograph having two columns, a conventional detector which supplies its output signal with the aid of a two-position commutator to a fixed-gain operational amplifier whose amplified signal is transmitted through a filter to a second commutatable operational amplifier having two gains, each of which corresponds to one of the two columns of the chromatograph and whose total output signal is balanced in a logarithmic amplifier while its error signal is supplied to a corresponding control amplifier, which, only during the opening of a time period, controls the correction of the voltage of the signal emitted from the detector by means of a motor coupled to a potentiometer; a timing and programming device which controls the time periods for "framing" the peaks" of the chromatogram and supplies the necessary action commands for the apparatus with the aid of several frequencies provided by an associated divider; a device for measuring and storing the maximum value of the analogue signal provided for each "peak" by the detector; a system for correcting, at the start of analysis on each column, the shifting from zero of the detector; a set of analogue memories, each relating to an analyzed constituent, each of which comprises a capacitor associated with a very high impedance amplifier and connected by de-multiplexing relays and an impedance converter to the output line of a digital-analogue converter whose input is connected by a switch to a buffer register effecting the reading of a zero-shifting register which is connected to a timing unit; a device for calibrating and linearizing the signal of the memories and a circuit for detecting faulty framing of a "peak" in an examination time period.

BRIEF DESCRIPTION OF THE DRAWINGS

The invention will now be described further by way of example with reference to the accompanying drawings in which:

FIG. 10 shows an example of a graph obtained on a graph recorder and demonstrating the percentage variations of the constituents included in a mixture of hydrocarbons and air taken as a sample from the drilling mud of an oil-well.

DESCRIPTION OF THE PREFERRED EMBODIMENT

Figure 1:
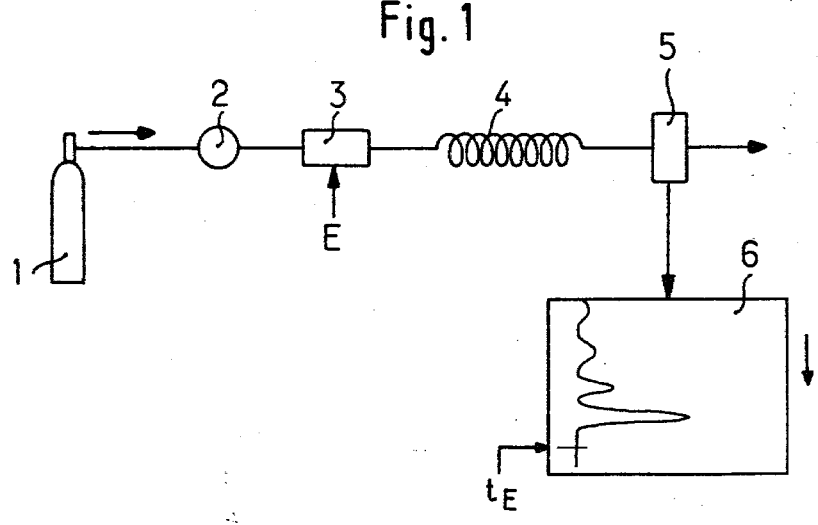
FIG. 1 shows a diagrammatic view illustrating the general arrangement of a chromatographic analysis apparatus of the type defined.

The chromatographic analysis apparatus of the type defined illustrated in FIG. 1 defines a gas path into which a pressure gas, hereinafter called "the carrier gas" discharges from a pressure reservoir 1 through a pressure control valve 2 to flow at constant flow-rate through sample injector 3, a chromatographic column 4 and a detector 5.

The injector 3 allows a sample E, a known volume of gaseous matter to be analyzed, to be injected into the carrier gas stream, whereupon the driving gas carries the sample E through the chromatographic column 4 and the constituents of the sample E from column 4 through detector 5.

The chromatographic column 4 comprises a helical tube containing a substance which reversibly adsorbs the constituents of sample E, thus delaying the passage of the constituents therethrough primarily due to the different molecular weight of the constituents, whereby the constituents are carried to the detector in ascending order of molecular mass.

Figure 2:
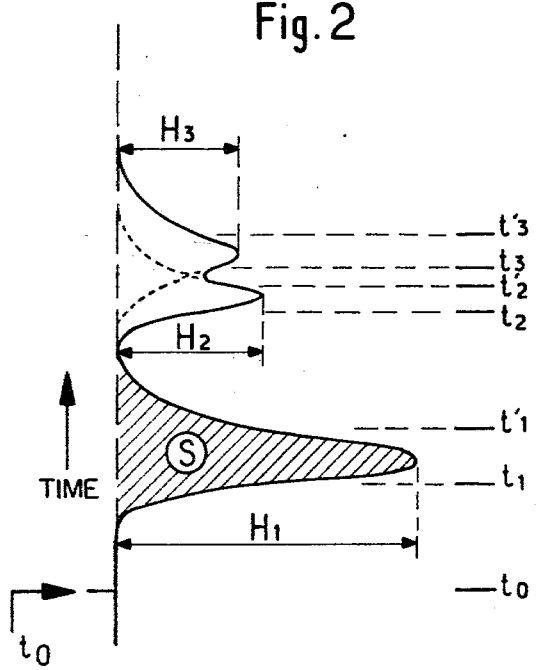
FIG. 2 shows one part of a graph obtained from the apparatus of FIG. 1 showing "peaks" each corresponding to a constituent contained in an examined sample of gaseous matter.

The detector 5 is sensitive to a property of the effluent emerging from the chromatographic column 4, or to a contrast between a physical property of the effluent and the carrier gas used and produces an electrical signal directly related to the concentration of constituent flow through the detector 5 and which signal is transmitted to a strip chart recorder 6, which supplies on paper a graph such as that partially illustrated in FIG. 2. As may be seen, the chart moves at a constant speed, the time axis being indicated by the vertical arrow and the recorder 6 thus produces a graph with the concentration of each constituent being designated by a "peak" individual thereto.

As stated hereinbefore the graph produced by the recorder 6 must be manually interpreted. In, for example, the analyzing of successive gas samples obtained from drilling mud, the gas may contain nitrogen and atmospheric oxygen and other light gases such as hydrogen or helium, as well as the following hydrocarbons which are to be analyzed quantitatively by chromatography:

methane: $C_1$
ethane: $C_2$
propane: $C_3$
isobutane: i. $C_4$
normal butane: n. $C_4$.

In such chromatography, two alternately functioning columns are used, one for separating the methane $CH_4$ from the other light gases (hydrogen, nitrogen, helium etc . . . ) and the other for separating the $C_2$ to $C_4$ hydrocarbons and possibly the $C_5$ pentanes from the light gases.

The two columns are commutated at the time of injection of the sample E by a system of values which may assume two positions, this system being well known and for reasons of simplicity being neither described nor illustrated in the present application except for the inversion relay which ensures its control.

As indicated above, the output of the detector 5 is utilized to draw a graph in which the presence of each constituent is represented by a more or less accentuated peak situated at a greater or lesser distance from the arrow $t_o$ which indicates the time of injection of a sample into device 3.

Each peak thus appears at a specific time called an elution time, after the injection of the sample at the time $t_o$ and its location must be effected precisely during the periods $t_1-t'_1$, $t_2-t'_2$, $t_3-t'_3$, etc. and in such a manner that their respective heights ($H_1$, $H_2$, $H_3$ . . . ) correspond to the maximum value of the signal supplied by the detector 5 for each constituent and characteristic thereof.

It is in fact known that the quantity of each constituent in the sample E may be evaluated from the surface S (shaded) which may be seen in FIG. 2 but when the recording of two constituents overlap, the dimension of this surface cannot be measured (see for example the overlap shown in dotted lines in FIG. 2) and so the height of the peaks ($H_1$, $H_2$, $H_3$ . . . ) is preferably measured in order to estimate the respective quantities of the constituents.

The height of the peaks also depends upon the reactivity of each constituent relative to the detector 5 and, in the particular application example chosen here—namely to determine the $C_1$ to $C_4$ hydrocarbon constituents of a gas occluded in mud from oil-well drilling, the reactivity of butane, for example, is basically four times higher than that of $CH_4$.

Figure 9:
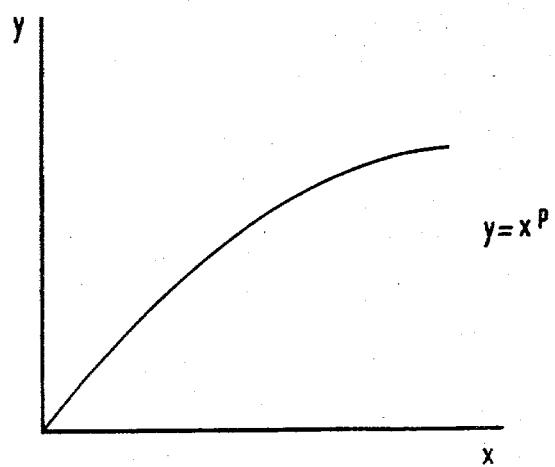
FIG. 9 shows a graph illustrating the function $x^p$ corresponding to the response supplied by the detector as a function of the percentage x of the gas.

Consequently, in the envisaged application, the measurement is effected within a range of concentration extending from 0.01% to 100% which, as may be seen in FIG. 10, necessitates the use of a logarithmic scale of four decades because the response of the detector is not a linear function of the percentage of the gaseous constituent in question but an empirical function whose graphic representation is the curve illustrated in FIG. 9 and which corresponds to the empirical operation $$y = x^p$$

in which p is an exponent which is determined experimentally.

The aim of the present invention is to afford an "automatic" processing of the different peaks $H_1$, $H_2$, $H_3$ corresponding to the different constituents of a gas sample and, in order to do this, to identify the peaks, to measure them and to store the maximum signal indicative of the concentration of the constituents.

Location of the peaks, as already explained, is effected by examination of the signal between different times $t'_1$ and $t_1$, $t'_2$ and $t_2$, $t'_3$ and $t_3$, etc . . . from the time origin corresponding to the "sample injection". These time examinations are sufficiently long as to allow for possible variations in the elution time caused by changes in the flow-rate of the carrier gas or in the temperature of the adsorbing agent but sufficiently short for there to be only one peak (see the top of FIG. 2), $t_3-t'_3$ being less than $t_1-t'_1$.

In the illustrated example of the invention, the detector 5 comprises a resistor R associated with a mixture of metals which act as oxidation catalysts and bring about an increase in the temperature which may be measured by the unbalanced signal of a conventional Wheatstone bridge in which the resistor is incorporated. Such an arrangement is illustrated in the left-hand portion of FIG. 3, this bridge comprising resistor R, a reference resistor R', fixed resistors $R_1$ and $R_2$ and a balancing potentiometer 7. The output signal of the detector is transmitted by way of the line 8 to an operational amplifier 9 of a fixed gain in the order of 1000, permitting appreciation of a signal of approximately one volt.

The amplified signal passes by way of the line 10 to a filter 11 which eliminates power frequency interference and is then supplied to an operational amplifier 12 having two gains which are commutatable and adjustable by means of resistors GAIN Si and SQ with the aid of an inverting relay 13 which is itself controlled in dependence upon the position of an inverting gate which determines the passage of the driving gas into one or other of the two chromatographic columns, necessary for analyzing the entire range of hydrocarbon constituents contained in, for example, the above described sample.

This two-gain amplifier 12 enables the signals from the detector 5 to be made comparable when the chromatograph is switched from one column to the other.

At the time of this switch, it is necessary, namely at the commencement of analysis for each column, to correct the drift from zero which the detector undergoes at the injection of each new sample.

Figure 3:
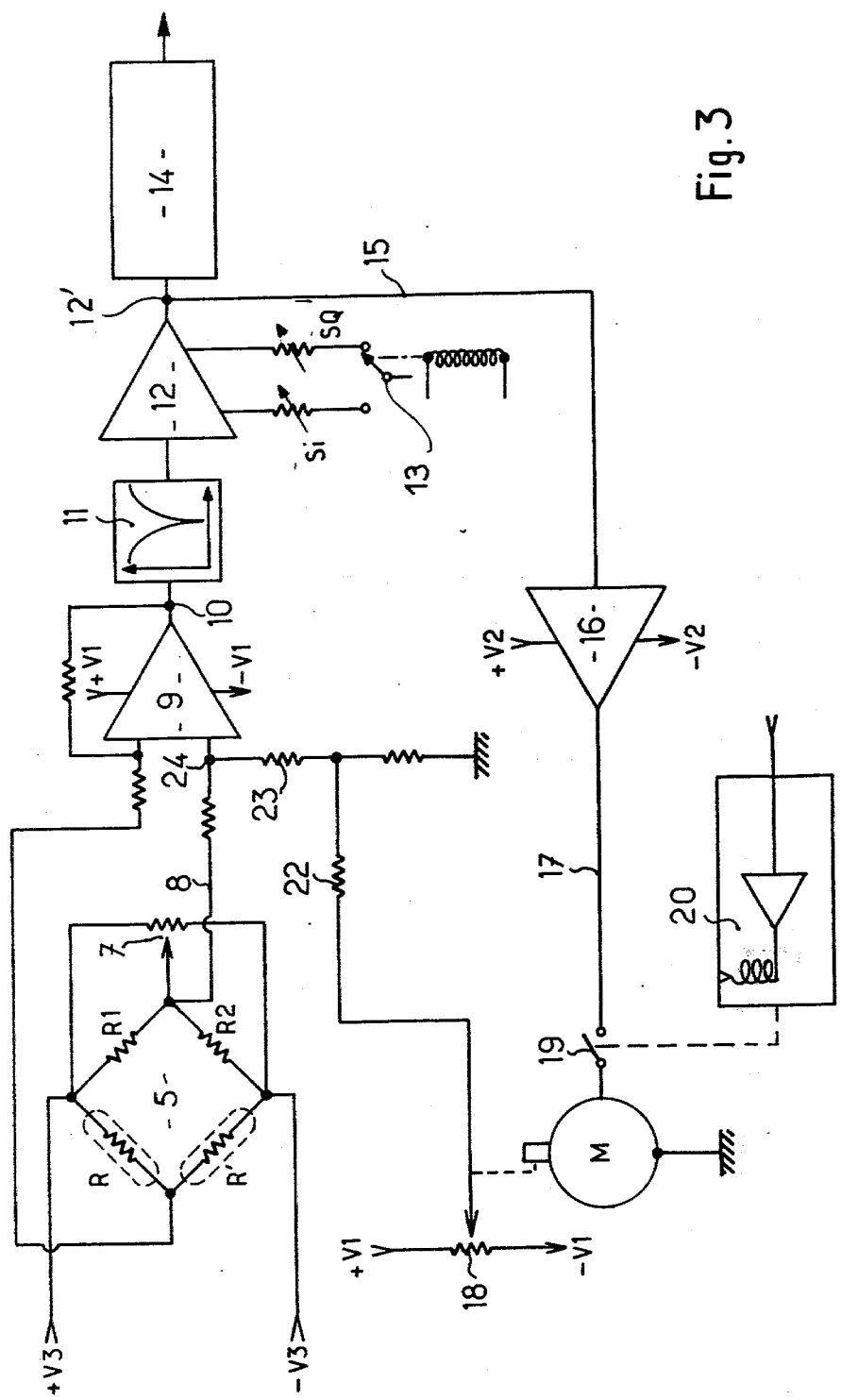
FIG. 3 shows a wiring diagram for the detector of a chromatographic analysis apparatus, illustrating the first phase of processing the signal supplied by the detector.

Thus, there is a period of approximately twenty seconds before the appearance of the first peak and for this correction the device illustrated in the lower portion of FIG. 3 is used. An "error signal", is taken at 12' from the output of the two-gain amplifier 12 upstream of a logarithmic amplifier 14 of a known type and by way of a conductor 15, the error signal passes to a control amplifier 16 whose output is supplied by way of the conductor 17 to the motor M of a multiturn potentiometer 18. The motor M which only operates during the period of about 20 seconds following injection of a sample E in device 3 and before the appearance of the first peak $H_1$, is controlled by a switch 19 which closes under the action of a relay 20 controlled by a monostable circuit 21 (FIG. 4) connected to the programmer which is described later. The voltage outputted by the potentiometer 18 (FIG. 3) is applied through a series of resistors 22 and 23 to a point 24 on the line 8 which directly supplies the signal from the detector 5 to the fixed-gain amplifier 9.

The logarithmic amplifier 14 converts the signal of the detector 5 according to the logarithmic function which, after correction and calibration as outlined hereinafter (FIG. 8), permits achievement of a scale of gas concentration of four decades from 0.01% to 100% (see FIG. 10).

Figure 4:
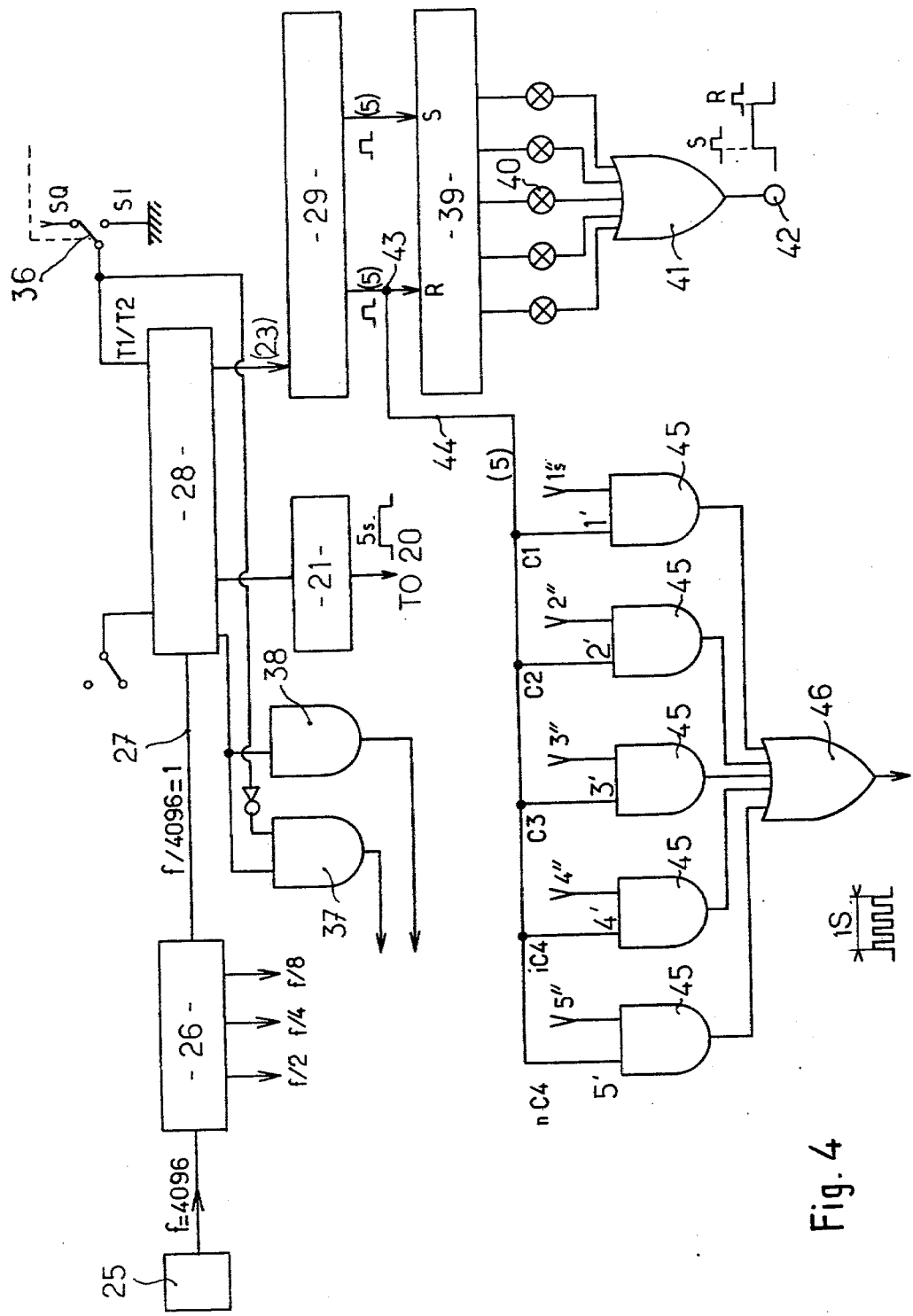
FIG. 4 shows a wiring diagram illustrating the timing and programming device for opening and closing the time windows with the commencement of the digitalization and digital-storage operations.

To open the time periods for examining the "peaks" and to give the necessary action commands, the invention provides a timing and programming device, illustrated diagrammatically in FIG. 4, comprising an oscillator 25 which produces a digital pulse signal (0 or 1) of a base frequency f of 4096 $H_z$ which is supplied to a 14-bit divider 26 having four outputs. Three of the outputs produce signals of the respective frequencies f/2, f/4 and f/8 which are used, as will be described later, for the circuits for digitalizing and maintaining analogue signals and the fourth output extends by way of a line 27 to a programmer generally designated 28 and supplies the latter with pulses at the rate of one per second.

Figure 5:
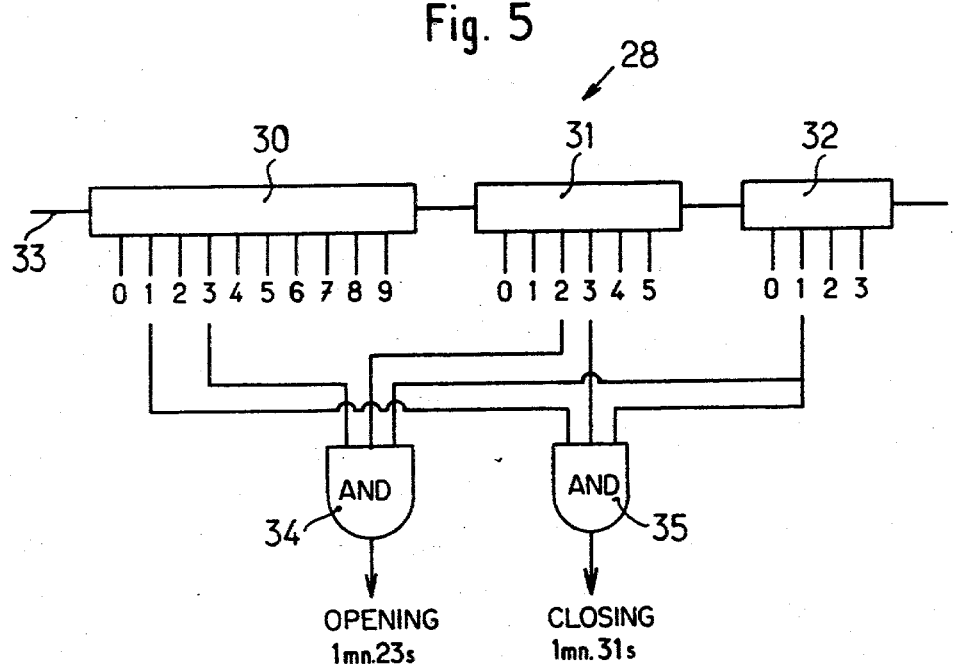
FIG. 5 is a diagrammatic view showing the detailed wiring of the programmer of FIG. 4.

The programmer 28, illustrated in greater detail in FIG. 5, controls the monostable circuit 21, which, in turn, controls the zero correction mentioned above, and also controls a decoder 29 which ensures start and termination of the time periods at the desired values. The programmer 28 also ensures inversion of the chromatograph columns.

The programmer 28 (see FIG. 5) comprises a decimal counter 30 having ten outputs numbered 0 to 9, a counter 31 with six outputs numbered from 0 to 5 and finally a counter 32 which is commutable to have either two or four outputs. The first counter 30 supplies the seconds, the second counter 31 the tens of seconds and the third counter 32 the minutes. These counters 30, 31 and 32 are of known type and provide an eletrical voltage at only one of their outputs at a time, this voltage being transferred to the succeeding output each time the counter receives a pulse at its input. The counter 30 counts the pulses arriving on line 33 and at the tenth pulse the voltage is transferred from the "nine" output to the "zero" output and a pulse is transmitted to the counter which resets itself to zero at the end of each sixth pulse transmitted to it.

To ensure decoding, "AND" gates designated 34 and 35 are used which ensure application of the control voltages at the desired moment, In the illustrated example, the "opening gate" 34, connecting to the terminal "1" of the counter 32, the terminal "2" of counter 31, and to the terminal "3" of counter 30, ensures opening at 1 minute 23 seconds counting from $t_o$ and the "closing" gate 35 connected to the terminal "1" of the counter 32, the terminal "3" of counter 31 and the terminal "1" of the counter 30 ensures "closure" at 1 minute 31 seconds, which gives 8 seconds for examining that peak expected between 1 minute 23 seconds and 1 minute 31 seconds from the time origin $t_o$.

As will be appreciated, a pair of gates are provided for each time period for examining a gaseous constituent to be measured and additional gates for the period for connecting zero by means of the monostable circuit 25 mentioned earlier.

The gate for switching the chromatographic columns, which are used alternatively, is controlled by an inverting relay 36, the control electromagnets receiving their voltage from "AND" gates 37 and 38 which are controlled by the programmer 28, one second after commencement of each cycle, whilst at the same time the minute counter 32 is switched either on 2 minutes for the first column or 4 minutes for the second column.

Figure 6:
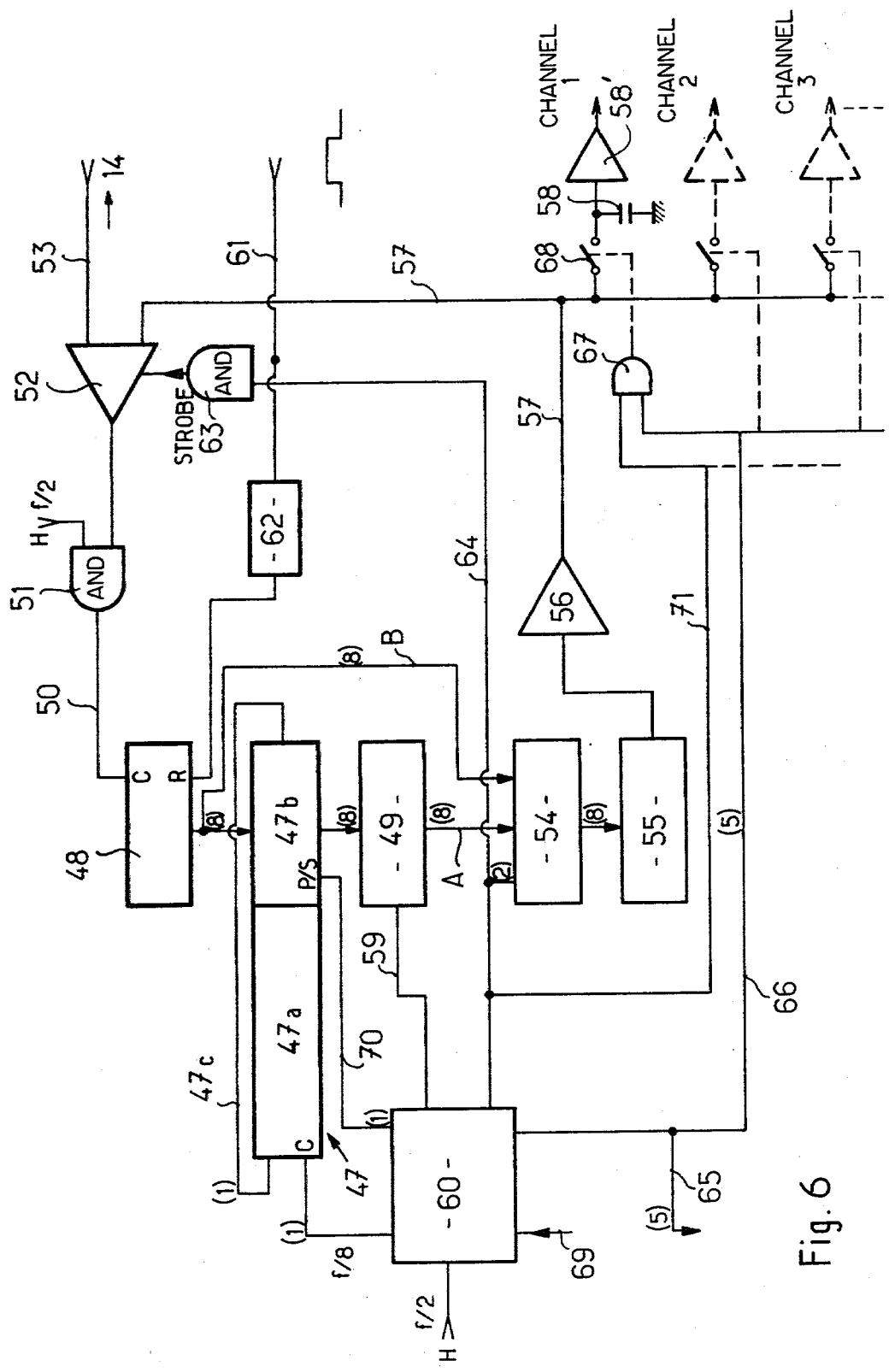
FIG. 6 is a diagrammatic view of a device for measuring and committing to memory the signal corresponding to each "peak" framed in a time window.

For simplicity, in appreciating the contents of FIGS. 4 and 6, the number of lines connecting elements of the circuits have been reduced to a minimum and the numbers in brackets placed next to the arrows on the lines connecting the different elements represent the number of connecting conductors. Thus, for example, there are 23 conductors connecting the programmer 28 to the decoder 29. Further and again for simplicity, only three of the channels are illustrated in FIG. 6.

The decoder 29 is connected to five rocker switches R/S forming the unit 39 (cf. FIG. 4) which are put in the S ("SET") position at the opening of the corresponding time period and then in the R ("RESET") position at the closure of this time period. The opening of each time period is indicated by indicating lights 40.

The rocker switches 39 are all connected to an "OR" gate 41 which, during opening of each time period supplies a "conversion order" signal to enable measurement of the height of the "peaks". This signal is taken at 42.

On each conductor connecting the decoder 29 to the five rocker switches of the group 39 there is provided a point 43 from which the signal is transmitted by a line 44, to one of the inputs 1', 2', 3', 4', 5' of five "AND" gates such as 45, each of which correspond to a $C_1$ to $nC_4$ gaseous constituent and whose other imputs 1", 2", 3", 4", 5" are connected to the demultiplexing system by a line having 5 conductors branching off from a similar line which connects a timing unit to gates whose output is connected each time to a demultiplexing relay connected to an analogue memory of a channel corresponding to the detected constituent.

As regards the output of these five gates 45, they are connected to the five inputs of an "OR" gate 46 which at the time of closure of the time period supplies a command to store the value of the corresponding chromatographic peak.

The device illustrated in detail in FIG. 6 is used for the measurement and storage of each peak during opening of the corresponding examination time period.

Figure 8:
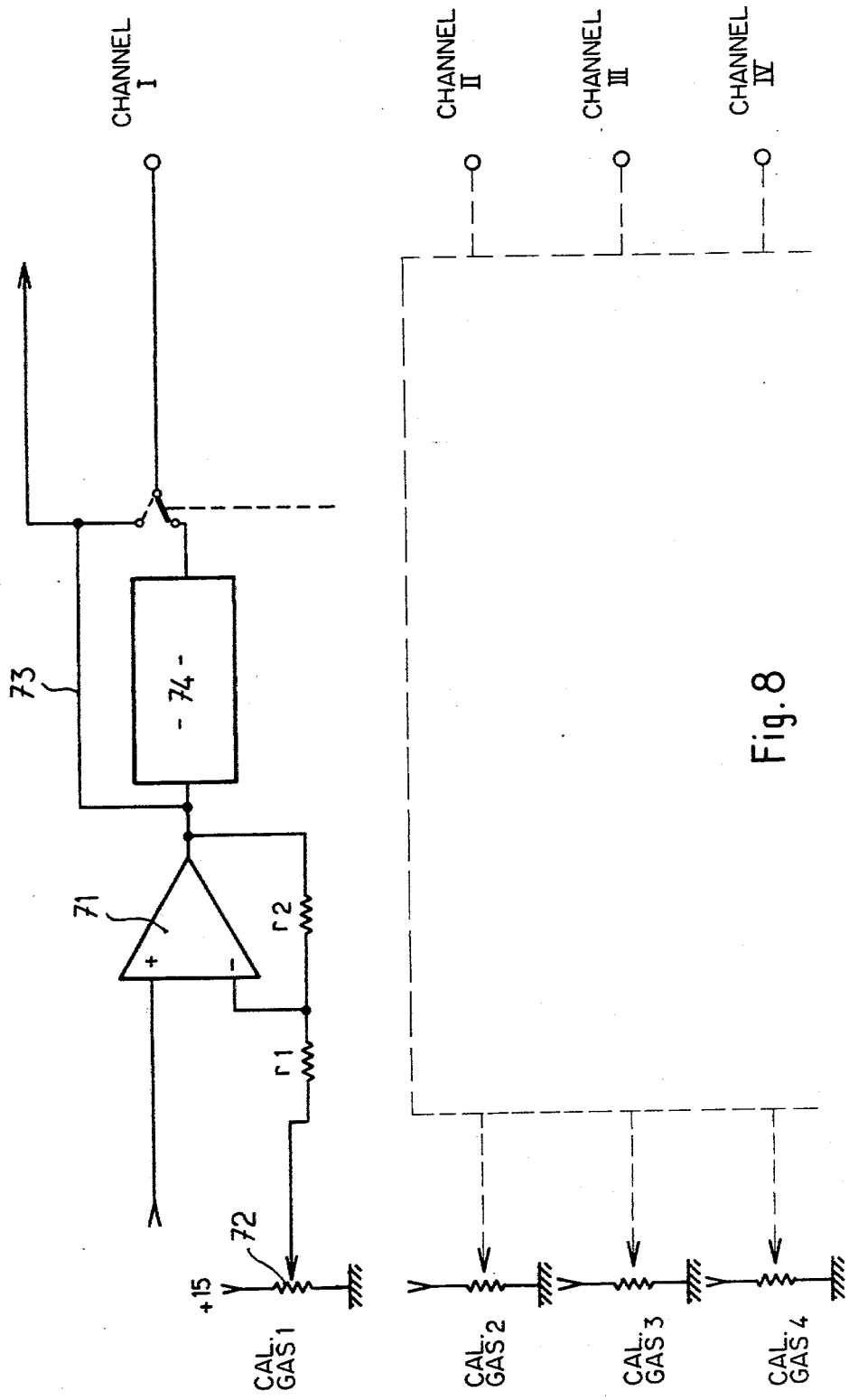
FIG. 8 shows a diagrammatic view of the final linearizing processing of the detector, calibration and smoothing of each stored value, the circuits of the channels II and following channels, identical to that of channel I, not being shown in detail for simplicity in the drawing.

As already stated, one of the basic intentions of the invention consists in digitalizing the signal provided by the chromatograph detector 5, and indicative of a "peak" corresponding to a constituent in the detector 5, by means of a comparison loop, a storing device and a transfer means for operating at regular intervals on an analogue memory, to "refresh" the memory before using the signal, i.e. before supplying the information to external systems (computer, recorder etc . . . ) with or without smoothing (cf. FIG. 8). To obtain this result there is provided a digital shift register which may permanently include five values, each corresponding to the "peak" of a constituent, each represented by an 8-bit word and capable of transferring them one by one to one of five analogue memories at the desired moment.

The shift register, generally designated by numeral 47, has a total capacity of 40 bits, and is subdivided into two segments 47a and 47b, the segment 47a capable of containing 4 words of 8 bits and the segment 47b one word of 8 bits. The first segment 47a can only function in series and the second segment 47b can function in a series with the segment 47a but also in parallel, i.e. it can either receive by a command from its input P/S a word from a counter 48 having a capacity of 8 bits or it can transmit a "whole" word which it contains to a buffer 49 of the same capacity. The input C of counter 48 is connected by a line 50 to the output of an "AND" gate 52 one of whose inputs is connected to the output f/2 of the frequency divider connected to the oscillator 25 and the other input is connected to a comparator amplifier 52 which receives the analogue signal produced by the logarithmic amplifier 14 by way of a line 53.

The register 47 is closed on itself by a recirculation conductor 47c, to allow the five words which it permanently contains to circulate in "conversation" under the effect of the shifting pulses provided at C of segment 47a at the frequency $f/8 = 512$ $H_z$ produced by a timing unit 60 whose function is described later. As regards charging of the buffer 49 and the control A/B of a direct transfer loop A and a comparison loop B, which comprises the comparator amplifier 52, the "AND" gate 51 allowing the introduction of timing pulses $f/2 = 2043$ $H_z$, the 8-bit input counter 48, a switch 54, a digital-analogue converter 55 formed by a network R/2R, an amplifier 56 serving as an impedance converter for supplying by way of a line 57 the comparator amplifier 52 and by way of demultiplexers the analogue memories such as 58, which are likewise controlled by the timing unit 60.

The analogue memories each comprise a capacitor 58 associated with a very high impedance amplifier 58'.

Since the shifting pulses enter at C in 47a at the frequency of 512, the shifting of the words therefore occurs every two milliseconds and a word of 8-bits requires $2 \times 8$ milliseconds or 16 milliseconds to advance a row.

The parallel circulation of the words occurs alternatively by means of two lines which are commutated by the switch 54.

The line B, comprising eight conductors, transfers the word included in the counter 48 directly to the converter 55 by way of the switch 54.

When a word is exactly framed in the counter 47b, it is transmitted to the register 49 and from there to the converter 55 by way of the switch 54. This transfer operation is controlled by one-conductor line 59 connecting the buffer register 49 to the timing unit 60.

The comparison loop used to measure and digitalize the maximum analogue signal closes itself on the comparator by way of the line 57 connected to the memories 58, this loop can only function during opening of one of the time periods associated with the different "peaks", the conversion order coming from 42 (FIG. 4) at the output of the gate 41 and being supplied by way of a line 61 which supplies on the one hand monostable circuit 62 for zero-setting (reset R) of the counter 48 and on the other hand an "AND" gate 63 whose input is connected by a line 64 (control A/B) to the timing unit 60 and whose output is connected to the comparator 52, thus forming a "STROBE" which inhibits functioning of the comparator if the conditions, namely time period open and line B open, are not simultaneously met.

The above system is so conceived that the "AND" gate 51 only receives a signal when the analogue voltage on the line 53 is greater than that of the line 57 by approximately 40 millivolts, this increment being constant in the entire area of variation of the analyzed signals.

It is therefore evident that, from the opening of an examination time period and after the appearance and measurement of the peak, a pulse is transmitted to the input C of the counter 48 by way of the line 50 and is transmitted by the line B through switch 54 to the converter 55; this pulse corresponding to the first number is converted on the reference line 57 into a voltage whose value is equal to the increment of the digital-analogue converter 55, which is itself identical to that of the comparator 52. There is therefore, balancing and cancellation of the output signal supplied to the "AND" gate 51, the transfer time in the loop B being less than a semi-period of the timing frequency $H = f/2$ supplied to the "AND" gate 51.

The second number will then appear in the input counter 48 as soon as the analogue signal arriving at 53 has passed the value of two increments, say $2 \times 40 = 80$ millivolts which, on the reference line 57, will again block the output of the comparator 52 until the signal has passed three increments and so on up to the maximum of the signal when the counter registers at the "maximum" with a unit equal to the value of the increment and perfectly determined.

When the time period is terminated, the value stored in the counter 48 is ready to be transmitted to the segment 47b of the zero-shifting register 47; this can only occur, however, when there is a whole word in the register 47b; this precise moment is determined by the timing unit 60 which acts as a chronometer and totals up the transfer pulses, causing a complete word to pass from the segment 47a to the segment 47b. For this purpose, the timing unit 60 is connected by a line 65 having five conductors connecting it to the inputs 1", 2", 3", 4" and 5" of the gates 45 illustrated in FIG. 4.

Branching off from this line 65, is a line 66 likewise having five conductors equal to the number of gaseous constituents to be measured which each lead to one of the inputs of the gates 67, their control output of the demultiplexing relays 68 connecting the analogue memories 58 to the line 57 which is connected by the impedance transformer 56 to the converter 55.

It is therefore evident from the above that the signal giving the order to store a word, i.e., the signal supplied by the gate 46, can only be transmitted if:
(1) the corresponding rocker switch 39 is re-set at zero (this corresponding to the closure of the corresponding time period) and
(2) the conductor relating to the lines 65 and 66 is energized, thus ensuring introduction of the word into the register 47b.

When these two conditions are satisfied, the gate 46 (FIG. 4) receives a signal from the corresponding gate 45 (according to the detected constituent) and transmits it to the timing unit 60 by way of the line 69 so that the latter effects the transfer to the register 47b of the word contained in the counter 48 at the moment when the word contained in the register 47b is exactly framed and may therefore pass into the buffer 49, this transfer is controlled by the line 70 which connects the input P/S to the timing unit 60 and receives a pulse every 16 milliseconds.

As regards the transmission to the analogue memories of the values stored for the five constituents during each chromatographic analysis, this is effected successively from the buffer register 49 into the different analogue memories 58 corresponding to the different channels (of which only three are shown in FIG. 6), each of them being naturally associated with gate 67 to a relay 68.

Transfer occurs during the phases of 8 milliseconds (see chronogram I of FIG. 7) when the switch 54 is directed towards the line A. The five conductors of the line 66 are energized in turn and each actuates the relay 68 corresponding to it as a complete word, transmitted from the buffer register 49 by the switch 54 to the converter 55, is translated by an analogue voltage, reproducing exactly and without distortion the maximum value of the corresponding recorded and digitalized "peak".

Since charging of the buffer 49 is effected every 16 milliseconds (see chronogram II, control P/S of FIG. 7), each memory is refreshed for 8 milliseconds every 80 milliseconds.

Besides the "referenced" signal supplied to them by the line 66, the gates 67 necessitate the position A by a branching 71 from the line 64 which connects the timing unit 60 to the "AND" gate 63.

Figure 7:
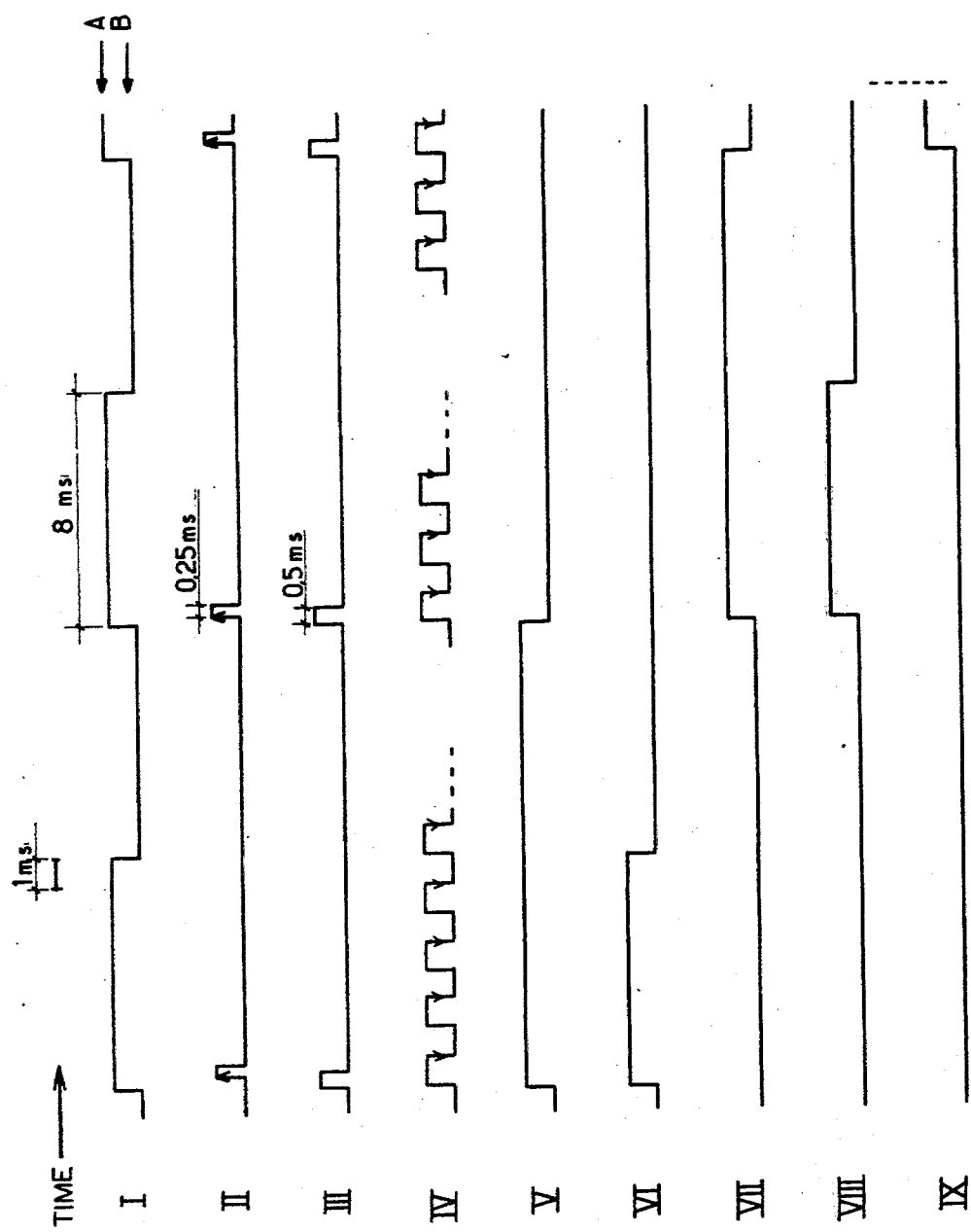
FIG. 7 shows a timing program illustrating the development of the different functions of the device.

FIG. 7 shows nine chronograms which retrace the control pulses supplied by the timing unit 60 for the different operations and for three time periods corresponding to three peaks.

Chronogram I alludes to the control A/B with inversion every 8 milliseconds (semi-period) at a frequency of f/64=4096/64 corresponding to a period of approximately 16 milliseconds.

Chronogram II retraces the control P/S effected for 0.25 ms every 16 ms.

Chronogram III relates to the pulses of 0.5 ms produced every 16 ms approximately and constituting the order for charging the buffer 49.

Chronogram IV illustrates the zero-shifting pulses produced at the frequency f/8=4096/8=512 Hz at the input C of the register 47 by the timing unit 60.

Chronogram V retraces the command produced in the lines 66 and 65 by the timing unit 60, in the relevant conductor corresponding to the first time period and to the first memory.

Chronogram VI illustrates charging of the analogue memory 58 of the channel I (FIG. 6).

Chronogram VII illustrates the command produced in the lines 66 and 65 by the timing unit 60, in the relevant conductor corresponding to the second time period and to the second memory.

Chronogram VIII illustrates charging of the second analogue memory corresponding to the second peak which appears (channel 2).

Chronogram IX retraces the command produced in the third conductor of the lines 66 and 65, etc.

The pulses for the other peaks, being easily deducible from the diagram, have not been shown for reasons of clarity in the drawing and especially because of its format.

From an examination of FIG. 7 in which the signals are square digital pulses, it may be seen for example for the chronogram II (command P/S) that there is an interval of 0.25 milliseconds every 16 milliseconds; however, this command is only validated by the signal which the gate 46 (FIG. 4) supplies at 69 to the timing unit acting by way of the line 70 upon the register 47b to clear it.

When the analogue values are recorded in the memories 58, these values are exploited for each channel by the device illustrated in FIG. 8. This figure only shows a circuit relating to one recorded value, for example for the methane contained in an analyzed gas sample.

In FIG. 8 it may be seen that the signal coming from each memory is linearized and smoothed.

Coefficient p figuring as an exponent in the function $$y = x^p$$

representing in practical terms the response of the detector 5 and being illustrated in FIG. 9. In fact, the response produced by chromatographic analysis (height of the peak) is not a linear function of the real percentage of the detected gaseous constituent.

Owing to the logarithmic amplifier 14 used (cf. FIG. 3), this function may be described in the form:

$$\log y = p \log x$$

so that by applying this coefficient p to the memories one will directly have the values representative of log x.

To do this, one uses an amplifier 71 (FIG. 8) and regulates its gain, as a function of the experimetally determined coefficient p, by adjusting the resistors $r_1$ and $r_2$ relative to one another.

To calibrate the signal, an electrical voltage is introduced for each constituent, said voltage being adjustable by means of resistors such as 72 provided in the circuit of the amplifier 71 which supplies the calibrated and linearized values either directly to an ordinator or through a smoothing filter 74 to a system which provides a diagram, such as that shown in FIG. 10.

This FIG. 10 shows, by way of indication, a graphic recording as a function of time of the variations which occur in the composition of a mixture of air and hydrocarbons and such as are continuously measured by extraction of the drilling mud from an oil-well using the device according to the invention, Δt representing the duration of a chromatographic measuring cycle.

On this curve, the recordings in stages correspond to the transcription of an unsmoothed signal.

As already indicated, variations in the elution time of the constituents as a result of, for example, changes in the supply of the carrier gas or the temperature of the absorbing agent can cause difficulties and may produce faulty "framing" of the peaks in the corresponding examination time periods.

To reduce this disadvantage, the chromatograph includes a detector which compares the input signals to the comparator 52.

In the course of the ascending slope of a peak, the signal of the detector arriving by way of the line 53 is always superior to the reference signal arriving at the output of the comparison loop by way of the line 57.

In contrast, on the descending slope of the peak, the analogue signal arriving at 53 is always inferior to the reference signal arriving by way of the line 57.

Consequently, the opening of a time period must be on the ascending slope and the difference between the signals arriving by way of 53 and 57 must be positive or at least zero if the peak is absent. On the other hand, at the termination of the time period, the difference must be negative or zero.

Figure 11:
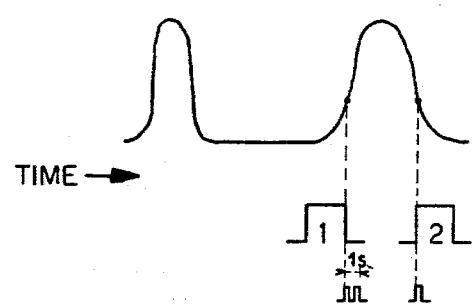
FIG. 11 shows a diagrammatic view illustrating the controlling of the framing of a "peak" in an examination time window and FIG. 12 shows a diagrammatic view of the device for detecting a fault in framing a "peak" in a window.

Referring to FIG. 11, it may be seen that the peak arrives too late if the time period is opened following the interval 1 and too soon if it is opened following the interval 2. In fact, at the end of the interval 1 the peak is ascending and at start of the interval 2 it is descending.

Figure 12:
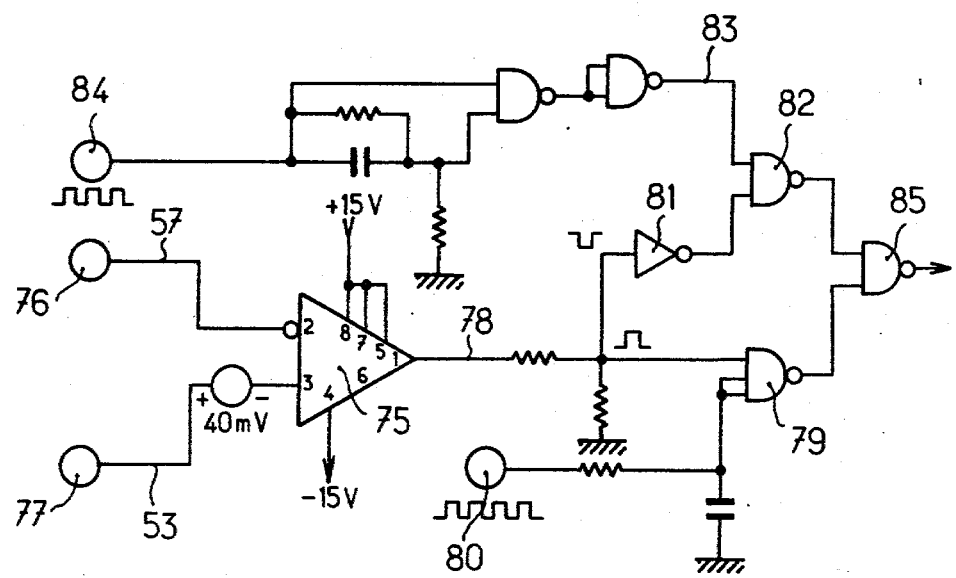

To reveal such a fault, the circuit shown in FIG. 12 is used which, in the event of faulty "framing" of a peak in a time period, produces an acoustic or light alarm signal, for example with the aid of a buzzer or luminous light.

As may be seen, the inputs "2" and "3" of a comparator 75 are connected by terminals 76 and 77 respectively to the lines 57 and 53 which are connected to the inputs of the comparator 52.

By way of the conductor 78 this comparator 75 supplies a comparison signal to one of the inputs of "NAND" gate 79 whose other input receives, by way of the terminal 80 connected to the output of the gate 46, the signal giving the order to store the value of the corresponding chromatographic peak. The comparison signal is also supplied by way of an inverter 81 to one of the inputs of another "NAND" gate 82 whose other input receives, by way of a line 83, the conversion order from a terminal 84 connected to the terminal 42 (FIG. 4) which is connected to the output of the gate 41 whose inputs are connected to the different rocker switches 39 actuated by the decoder 29 which controls the opening and closing of the time period.

The outputs of the gates 79 and 82 are connected to the inputs of the "NAND" gate 85 producing the signal which supplies a buzzer and/or a light alarm (not shown).

This comparator 75 functions by increments of 4-millivolts and to the specialist the functioning of the circuit shown in FIG. 12 is easily comprehensible without the need for more detailed explanation.

Whilst the present invention has been described by way of example with reference to a specific embodiment the example is in no way restrictive and many modifications and variations could be undertaken without in any way departing from the scope of the appended claims. Thus for example, the apparatus could be adapted to detect and record more or less than five peaks in the case of a gaseous mixture comprising a greater or lesser number of constituents to be measured. In such cases, a greater or lesser number of rocker switches and therefore gates would be provided as well as a shift register having a capacity of n × 8-bits n, being the number of constituents of the mixture, and a quantity of memories and demultiplexing relays corresponding to the number of constituents.

It would obviously be necessary to adapt the frequencies supplied by the oscillator to the rhythms of the pulses to be supplied and to the width of the intervals.

I claim:

1. A method for processing the signal produced by the detector of a chromatographic analysis apparatus having a gaseous matter sample flowing through the detector thereof for testing purposes and containing at least one gaseous constituent therein, comprising the steps of:

monitoring the detector signal obtained during a sample analysis over a fixed time period, said fixed time period spaced from a time origin so as to include the approach to and fall from the maximum concentration of one of the at least one gaseous constituents flowing through the detector;

detecting the maximum amplitude of the detector signal indicative of the concentration of one of the at least one constituents within the time period;

storing the value of the maximum amplitude signal in an afferent index memory and utilizing the stored value to generate a value corresponding to the proportion of one of the at least one constituents with respect to the gaseous matter sample flowing through the detector within the time period.

2. A method as claimed in claim 1, wherein the gaseous sample comprises a plurality of constituents, further comprising the steps of:

monitoring the detector signal over a plurality of time periods during a sample analysis, said time periods being differently spaced from the start time origin with respect to each other, whereby the approach to and fall from the maximum concentration of the plurality of constituents passing through the detector occur during different time periods;

detecting the maximum amplitude of the signal indicative of the concentration of each of the plurality of constituents during its respective time period and processing each of the signals to generate values corresponding to the proportions of respective detected constituents with respect to the entire gaseous matter sample.

3. A method as claimed in claim 1, wherein the detector supplies an analog signal, further comprising the steps of:

digitalizing each detected signal corresponding to the maximum concentration of a constituent;

transmitting each digitalized signal to a digit register and applying an analog signal corresponding to each digitalized signal at regular intervals to one or more analog memories for storage therein;

and supplying each storage signal indicative of the proportion of each constituent with respect to the gaseous matter sample to at least one of an external processing system, display system, or recording system.

4. A method for analysing gaseous matter by chromatographic analysis, comprising the steps of: injecting a gaseous matter sample into a gas stream; passing the gas stream bearing said sample through a material selected to delay passage of the gas constituents of the sample in dependence upon their molecular structure; detecting the presence of the gas constituents at a detector downstream of said material, said detector being arranged to emit a signal related to the intensity of each of selected constituents of said gas, as each said selected constituent passes through the detector; monitoring the detector signal obtained over a number of fixed periods of time, each spaced from that time at which the sample was injected into said gas stream as to include the approach to and fall from maximum concentration of one said selected gaseous constituent individual to that time period; detecting the maximum amplitude of the signal indicative of the concentration of each constituent within its respective time period, storing each maximum amplitude value in a afferent index memory and utilizing the stored maximum amplitude values to generate values directly representative of the proportions of the constituents flowing through the detector within said time periods.

5. Apparatus for processing the detector signal of a chromatographic analysis apparatus comprising, in combination:
   a timing and programming device for initiating and terminating time periods each of which occurs whilst the detector is transmitting a signal indicative of the concentration of a constituent to be measured;
   a device for digitalizing the detected signal transmitted during each time period and for storing the maximum value thereof which is respectively indicative of the concentration of each constituent to be measured;
   an analogue memory corresponding to each constituent to be measured;
   a device for calibrating and linearizing the signal stored in said memory, and means for outputting said signal.

6. Apparatus as claimed in claim 5, wherein the programming device comprises, in combination, a counter having ten outputs, a counter having six outputs and a counter having one of either two or four outputs; the programming device supplying the voltage for opening and closing the time periods and comprising a decoder connected to five pairs of "AND" gates; said programming device connected to an oscillator by means of a frequency divider.

7. Apparatus as claimed in claim 6, further comprising a respective light for each time period, and a respective switch connected to each light for illuminating its respective light during its relevant time period, each of said switches being controlled by said decoder, said decoder further connected to an "OR" gate for generating a "conversion order" signal enabling digitalization and measurement of the maximum value of the signal indicative of the concentrations of the constituents and further connected to one of the inputs of a plurality of "AND" gates whose outputs are connected to an "OR" gate which, at each closure of a time period, generates an order to store the maximum signal value in said memory.

8. Apparatus as claimed in claim 5, wherein linearization of the signal available at the output of said analogue memory is effected by an amplifier whose gain is adjusted as a function of the response which is supplied by a logarithmic amplifier for balancing said signal and which takes the form $$\log y = p \log x$$

y being the response of the detector and x being the percentage of the constituent detected in the corresponding time period.

9. Apparatus as claimed in claims 5 or 8, wherein the device for digitalizing and storing the maximum value of the detector signal indicative of the concentration of a constituent comprises a single digital-analogue converter, which effects the conversions for all the detected constituents, said converter being inserted in a comparison loop connected to said analogue memory and comprising a comparator amplifier, an "AND" gate receiving a pilot frequency f/2 from a divider connected to an oscillator of said programming device, an 8-bit counter, a switch connected to a buffer register and an amplifier serving as an impedance converter for supplying the comparator amplifier and analogue memory.

10. Apparatus for processing the detector signal of a chromatographic analysis apparatus including two columns for gas analysis, comprising in combination;
   a timing and programming device for initiating and terminating time periods each of which occurs whilst the detector is transmitting a signal indicative of the concentration of a constituent to be measured;
   a comparison loop for digitalizing the maximum detector signal emitted during each of said time periods and for storing each of said digitalized signals in a counter;
   a shift register for storing a plurality of said digitalized signals; a digital to analog converter connected to a plurality of analog memories for storing analog values indicative of the concentration of each constituent to be measured.

11. Apparatus as claimed in claim 10, wherein the two columns are switched by an inverting relay which, in dependence upon the output of a gate, controls electromagnets with "AND" gates connected to the programming device, said relay simultaneously ensuring the selection of different lengths of time cycles for each column, an inverter being provided between an input of one of said "AND" gates and the relay.

12. Apparatus as claimed in claim 10, further comprising a circuit for detecting incorrect time location of a generated time period and for indicating such incorrect location.

13. Apparatus as claimed in claim 11, wherein the programming device comprises in combination a counter having ten outputs, a counter having six outputs and a counter having one of either two and four outputs, and said programming device supplies the voltage for opening and closing the time periods with a decoder connected to five pairs of "AND" gates, said programmer being connected to an oscillator by means of a divider for controlling said memory circuits.

14. Apparatus as claimed in claim 12, further comprising a light for each time period and a switch for illuminating each light during its relevant time period, said switches being controlled by said decoder; said decoder further being connected to an "OR" gate for supplying a "conversion order" signal permitting measurement of the strength of the signal indicative of the concentrations of each of said constituents, and further supplying to one of the inputs of "AND" gates whose outputs are connected to an "OR" gate which, at each closure of a time period, supplies the order to store the converted signal value in one of said memories.

15. Apparatus as claimed in claim 10, wherein the device for measuring and storing the value of the detector signal indicative of the concentration of a constituent comprises a single digital-analogue converter, which effects the conversions for all the detected constituents, said converter being inserted in said comparison loop connected to the analogue memories and comprising a comparator amplifier, an "AND" gate receiving a pilot frequency f/2 from a divider connected to an oscillator of the programmer, an 8-bit counter, a switch connected to a buffer register and an amplifier serving as an impedance converter for supplying the comparator amplifier and analogue memories.

16. Apparatus as claimed in claim 10, in which linearization of the signal available at the output of said analogue memory is effected by an amplifier whose gain is adjusted as a function of the response which is supplied by a logarithmic amplifier for balancing said signal and which takes the form $$\log y = p \log x$$

y being the response of the detector and x being the percentage of the constituent detected in the corresponding time period.

17. Apparatus comprising in combination a chromatograph having two columns and means for the interpretation of the signal supplied by the detector of a chromatograph, said means comprising a two-position commutator for receiving the output signal from the detector and extending said signal to a fixed gain operational amplifier whose amplified signal is transmitted through a filter to a second commutable operational amplifier having two gains, each of which corresponds to one of the two columns of the chromatograph and whose total output signal is balanced in a logarithmic amplifier while its error signal is supplied to a corresponding control amplifier which, only during the opening of a time period, controls the correction of the voltage of the signal emitted from the detector by means of a motor coupled to a potentiometer; a timing and programming device which controls the time periods for "framing" the "peaks" of the chromatogram and supplies the necessary action commands for the apparatus with the aid of several frequencies provided by an associated divider; a device for measuring and memorizing the maximum value of the analogue signal provided for each "peak" by the detector; a system for correcting, at the start of analysis on each column, the shifting from zero of the detector; a set of analogue memories, each relating to an analyzed constituent, each of which comprises a capacitor associated with a very high impedance amplifier and connected by de-multiplexing relays and an impedance converter to the output line of a digital-analogue converter whose input is itself connected by a switch to a buffer register effecting reading of a zero-shifting register which is connected to a timing unit; a device for calibrating and linearising the signal of the memories and a circuit for detecting faulty framing of a "peak" in an examination time period.

* * * * *